United States Patent
Yaroshenko et al.

(10) Patent No.: US 11,421,984 B2
(45) Date of Patent: Aug. 23, 2022

(54) TESTING OF CURVED X-RAY GRATINGS

(71) Applicant: KONINKLIJKE PHILIPS N.V., Eindhoven (NL)

(72) Inventors: Andriy Yaroshenko, Garching (DE); Thomas Koehler, Norderstedt (DE); Hanns-Ingo Maack, Norderstedt (DE); Matthias Teders, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/955,978

(22) PCT Filed: Dec. 11, 2018

(86) PCT No.: PCT/EP2018/084257
§ 371 (c)(1),
(2) Date: Jun. 19, 2020

(87) PCT Pub. No.: WO2019/121129
PCT Pub. Date: Jun. 27, 2019

(65) Prior Publication Data
US 2020/0305810 A1   Oct. 1, 2020

(30) Foreign Application Priority Data
Dec. 19, 2017 (EP) .................... 17208415

(51) Int. Cl.
*G01B 11/255* (2006.01)
*A61B 6/00* (2006.01)
(Continued)

(52) U.S. Cl.
CPC .............. *G01B 11/255* (2013.01); *A61B 6/58* (2013.01); *G01B 11/2518* (2013.01);
(Continued)

(58) Field of Classification Search
CPC .............. G01B 11/255; G01B 11/2518; G01B 11/2441; G01B 11/2443; G01N 21/95684;
(Continued)

(56) References Cited

U.S. PATENT DOCUMENTS

| 4,606,640 A | 8/1986 | Hirst |
| 2009/0168026 A1* | 7/2009 | Chen ...................... G03B 21/60 353/20 |

(Continued)

FOREIGN PATENT DOCUMENTS

| CN | 106441823 A | 2/2017 |
| DE | DD257495 A1 | 6/1988 |

OTHER PUBLICATIONS

PCT International Search Report, International Application No. PCT/EP2018/084257, dated Mar. 21, 2019.
(Continued)

*Primary Examiner* — Michael P LaPage
(74) *Attorney, Agent, or Firm* — Larry Liberchuk

(57) ABSTRACT

The present invention relates to a method, and a corresponding device, for testing a radius of curvature and/or for detecting inhomogeneities of a curved X-ray grating for a grating-based X-ray imaging device. The method comprises generating a beam of light diverging from a source point, propagating along a main optical axis and having a line-shaped beam profile. The method comprises reflecting the beam off a concave reflective surface of the grating. A principal axis of the concave reflective surface coincides with the main optical axis and the source point is at a predetermined distance from a point where the main optical axis intersects the concave reflective surface. The method comprises determining whether a projection of the reflected beam in a plane at or near the source point is present outside a central region around the source point, in which an absence of this projection outside the central region indicates that a (Continued)

radius of curvature of the concave reflective surface corresponds to the predetermined distance and/or that the reflective surface is substantially homogeneously curved along a curve formed by the beam impinging on the concave reflective surface.

12 Claims, 2 Drawing Sheets

(51) Int. Cl.
| | |
|---|---|
| *G21K 1/06* | (2006.01) |
| *G01B 11/25* | (2006.01) |
| *G01N 21/55* | (2014.01) |
| *G01N 21/956* | (2006.01) |
| *G01M 11/00* | (2006.01) |
| *G01N 23/041* | (2018.01) |

(52) U.S. Cl.
CPC ........... *G01M 11/005* (2013.01); *G01N 21/55* (2013.01); *G01N 21/95684* (2013.01); *G21K 1/06* (2013.01); *A61B 6/4085* (2013.01); *A61B 6/484* (2013.01); *G01N 23/041* (2018.02); *G21K 2201/064* (2013.01); *G21K 2207/005* (2013.01)

(58) Field of Classification Search
CPC ................. G01N 21/55; G01N 23/041; G01N 2021/9511; G01N 2223/315; G21K 1/06; G21K 2207/005; G21K 2201/064; G21K 1/025; G21K 1/067; A61B 6/58; A61B 6/484; A61B 6/4085; G01M 11/005
See application file for complete search history.

(56) References Cited

U.S. PATENT DOCUMENTS

| | | | |
|---|---|---|---|
| 2012/0002785 A1* | 1/2012 | Kaneko | G21K 1/067 378/62 |
| 2013/0259194 A1* | 10/2013 | Yip | A61B 6/502 378/37 |
| 2015/0316494 A1* | 11/2015 | Teshima | A61B 6/4035 378/36 |
| 2015/0318144 A1* | 11/2015 | Anan | G01N 23/2252 250/306 |
| 2016/0363440 A1 | 12/2016 | Stites | |
| 2018/0217071 A1* | 8/2018 | Chen | G01N 23/041 |
| 2019/0316898 A1* | 10/2019 | Kim | G01B 11/2441 |
| 2021/0093273 A1* | 4/2021 | Kotani | G21K 1/06 |

OTHER PUBLICATIONS

Rufino Diaz-Uribe et al., "Cylindrical Lenses: Testing and Radius of Curvature Measurement", Applied Optics, vol. 25, No. 10, May 15, 1986 (May 15, 1986), pp. 1707-1709.
Cornejo-Roorıguez A. et al., "Measurement of Radii of Curvature of Convex and Concave Surfaces Using a Nodal Bench and He—Ne Laser", Applied Optics, vol. 19, No. 11, Jun. 1, 1980 (Jun. 1, 1980), pp. 1743-1745.
Diaz-Uribe R. et al., "Profile Measurement of a Conic Surface, Using a He—Ne Laser and a Nodal Bench", Applied Optics, vol. 24, No. 16, Aug. 15, 1985 (Aug. 15, 1985), pp. 2612-2615.
Anderson J. A. et al., "Ronchi's Method of Optical Testing", Astrophysical Journal., vol. 70, Oct. 1929 (Oct. 1929), pp. 175-182.
Wang Y.P. et al, "A Novel Long Period Fiber Grating Sensor Measuring Curvature and Determining Bend-Direction Simultaneously", IEEE Sensors Journal, vol. 5, No. 5, pp. 839-843, Oct. 2005.
Lin Y.H. et al., "Estimation of Radius of Curvature Using Reflected-Spot Method", 2015 IEEE International Instrumentation and Measurement Technology Conference (I2MTC) Proceedings.

\* cited by examiner

TESTING OF CURVED X-RAY GRATINGS

FIELD OF THE INVENTION

The invention relates to the field of grating-based X-ray imaging. More specifically it relates to a method and device for testing a radius of curvature and/or detecting inhomogeneities of a curved grating for a phase-sensitive and/or dark-field X-ray imaging device.

BACKGROUND OF THE INVENTION

Grating-based X-ray imaging techniques, e.g. phase-sensitive X-ray imaging and X-ray scatter imaging, e.g. X-ray phase contrast imaging and/or the related scatter-sensitive dark-field imaging, are imaging modalities known in the art that enables the acquisition of an image representative of local changes in refractive index and/or in ultra-small-angle scattering of an object of interest, e.g. through the body of a subject. Phase contrast X-ray imaging and/or dark-field imaging can provide additional diagnostic information in clinical X-ray imaging when compared to conventional X-ray imaging techniques, for example in chest radiography, mammography, and/or other clinical applications.

In order to detect phase shifts, phase information may need to be transformed into local variations of x-ray intensity, which can be recorded by an image detector. Furthermore, a dark-field image, representative of ultra-small-angle scattering, e.g. at a micrometer or sub-micrometer scale, can be obtained by a similar, or substantially the same, configuration as used for detecting a phase contrast image.

It is known in the art to enable the acquisition of an x-ray phase contrast image and/or a dark field image by using a grating interferometer system. Such grating interferometer system may comprise at least a phase grating and an analyser grating. In clinical applications, the grating interferometer system may typically consist of three gratings. Such gratings may usually have a period of a few micrometers and a height of several hundred micrometers, to achieve a required absorption. This high aspect ratio typically requires the grating to be adapted to the X-ray beam shape, e.g. a cone beam, to avoid disadvantageous shadowing effects.

To achieve an adaptation of the grating to the beam shape, e.g. to a cone beam geometry, it is known in the art to physically bend the grating. However, such bending process has to be carefully controlled to ensure that the bending radius and homogeneity of the grating is within tight tolerance limits, since a mismatch of the grating radius to the imaging system configuration and/or inhomogeneities in the grating can lead to significant imaging artefacts.

Furthermore, the shape of the deformed grating can evolve over time, e.g. during use of the imaging system. For example, stresses, such as stresses due to mechanical manipulation, accidental impacts and/or thermal interactions, can change the shape of the grating over time. Therefore, a need exists in the art for a method of calibration and validation of the radius and/or homogeneity of the grating during manufacture, installation, quality control and/or maintenance of the grating and the system in which it is installed.

SUMMARY OF THE INVENTION

It is an object of embodiments of the present invention to provide a good and efficient device and method for testing a radius of curvature and/or detecting inhomogeneities of a curved grating for a grating-based imaging device, e.g. a phase-sensitive and/or dark-field X-ray imaging device.

It is an advantage of embodiments of the present invention that inhomogeneities in the curvature of the curved grating can be easily and/or quickly diagnosed.

It is an advantage of embodiments of the present invention that deviation of the radius of curvature of the curved grating from a predetermined radius specification can be easily and/or quickly diagnosed.

It is an advantage of embodiments of the present invention that a method for testing the curved grating can be easily implemented in the field, e.g. in a quality control or maintenance procedure executed on-site, e.g. in a hospital department where the curved grating is installed in the X-ray imaging device.

It is an advantage of embodiments of the present invention that a compact and portable device is provided for testing the curved grating.

It is an advantage of embodiments of the present invention that imaging artefacts in images generated by a phase-sensitive and/or dark-field X-ray imaging device, due to properties of a curved grating in that device, can be easily diagnosed.

The above objective is accomplished by a method and device according to the present invention.

In a first aspect, the present invention relates to a method for testing a radius of curvature and/or detecting inhomogeneities of a curved X-ray grating for a grating-based X-ray imaging device, e.g. a phase-sensitive and/or dark-field X-ray imaging device. The method comprises generating a beam of light. The beam of light diverges from a source point, propagates along a main optical axis of propagation of the beam and has a beam profile shaped as a line. The method comprises reflecting the beam of light off a concave reflective surface of the curved X-ray grating. A principal axis of the concave reflective surface substantially coincides with the main optical axis and the source point is at a predetermined distance from a point where the main optical axis intersects the concave reflective surface. Thus, the main optical axis coincides with the principal axis of the concave reflective surface, or, in other words, the main optical axis is formed by a line through the source point and through the center of the curved grating surface, this line being oriented normal to the curved grating surface at the center of the curved grating surface.

The method comprises determining whether a projection of the reflected beam of light in a plane at or near the source point is present outside a central region around the source point, in which an absence of the projection outside the central region indicates that a radius of curvature of the concave reflective surface substantially corresponds to the predetermined distance and/or that the reflective surface is substantially homogeneously curved along a curve formed by the beam of light impinging on the concave reflective surface, e.g. by the line-shaped profile projected onto the concave reflective surface.

Where reference is made in the present description to a curved X-ray phase grating, it shall be clear that this may comprise any type of curved X-ray grating for grating-based X-ray imaging, such as a curved X-ray coded-aperture array. For example, such coded-aperture arrays are well-known in the art, e.g. as known for implementing a coded-aperture technique for allowing x-ray phase contrast imaging with conventional sources.

In a method in accordance with embodiments of the present invention, the plane at or near the source point may be oriented perpendicular to the main optical axis.

In a method in accordance with embodiments of the present invention, the beam of light may comprise generating the beam of light comprising light in at least part of the visible and/or ultraviolet spectrum using a laser light source.

In a method in accordance with embodiments of the present invention, the beam of light may comprise forming the beam profile shaped as a line using an optical lens, an optical mirror or an optical assembly.

A method in accordance with embodiments of the present invention may comprise polishing a concave surface of the curved X-ray grating to form the concave reflective surface.

Alternatively, or additionally, a method in accordance with embodiments of the present invention may also comprise bonding a reflective material to the concave surface to obtain the concave reflective surface. For example, a thin metal foil, e.g. an aluminium foil, may be bonded to the surface to achieve reflectiveness. It is a further advantage that such foil may also act as a protective layer for the grating.

In a method in accordance with embodiments of the present invention, the central region may have a diameter, around the source point, of less than 20 times the width of the beam profile shaped as a line.

A method in accordance with embodiments of the present invention may comprise providing a projection screen in the plane at or near the source point.

In a method in accordance with embodiments of the present invention, reflecting the beam of light off the concave reflective surface may comprise projecting the beam of light through a hole in the projection screen.

A method in accordance with embodiments of the present invention may comprise adjusting the predetermined distance between the point where the main optical axis intersects the concave reflective surface and the source point, in which the step of reflecting the beam of light off the concave reflective surface may be repeated for the adjusted distance, and in which the step of determining whether the projection of the reflected beam in the plane at or near the source point is present outside the central region around the source point may be repeated for the adjusted distance.

A method in accordance with embodiments of the present invention may comprise repeatedly adjusting the predetermined distance to determine the radius of curvature of the concave reflective surface as corresponding to the adjusted distance for which the projection of the reflected beam in the plane is absent outside the central region around the source point and/or for which the projection is contained in the smallest region, e.g. relative to other evaluations for the other tested distances, around the source point in the plane.

A method in accordance with embodiments of the present invention may comprise continuously adjusting the predetermined distance between the point where the main optical axis intersects the concave reflective surface and the source point, and continuously monitoring changes in the projection to determine the radius of curvature.

A method in accordance with embodiments of the present invention, may comprise rotating the beam profile shaped as a line of the generated beam of light such as to evaluate the radius of curvature and/or inhomogeneities of the curved grating along different lines projected by the beam over the concave reflective surface.

In a second aspect, the present invention relates to a device for testing a radius of curvature and/or detecting inhomogeneities of a curved X-ray grating for a phase-sensitive and/or dark-field X-ray imaging device. The device comprises a laser light source adapted for generating a beam of light that diverges from a source point, propagates along a main optical axis of propagation of the beam and has a beam profile shaped as a line. The device comprises a projection screen for positioning in a plane at or near the source point to determine whether a projection of a reflected beam of light is present outside a central region around the source point, when the reflected beam of light is created by reflecting the beam of light off a concave reflective surface of the curved X-ray grating such that a principal axis of the concave reflective surface substantially coincides with the main optical axis.

In a device in accordance with embodiments of the present invention, the light source may be fixed to the projection screen, e.g. such that, in use of the device, such as in a use in accordance with a method of embodiments of the first aspect of the present invention, the source point lies in or near the plane.

In a device in accordance with embodiments of the present invention, the projection screen may be collapsible.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
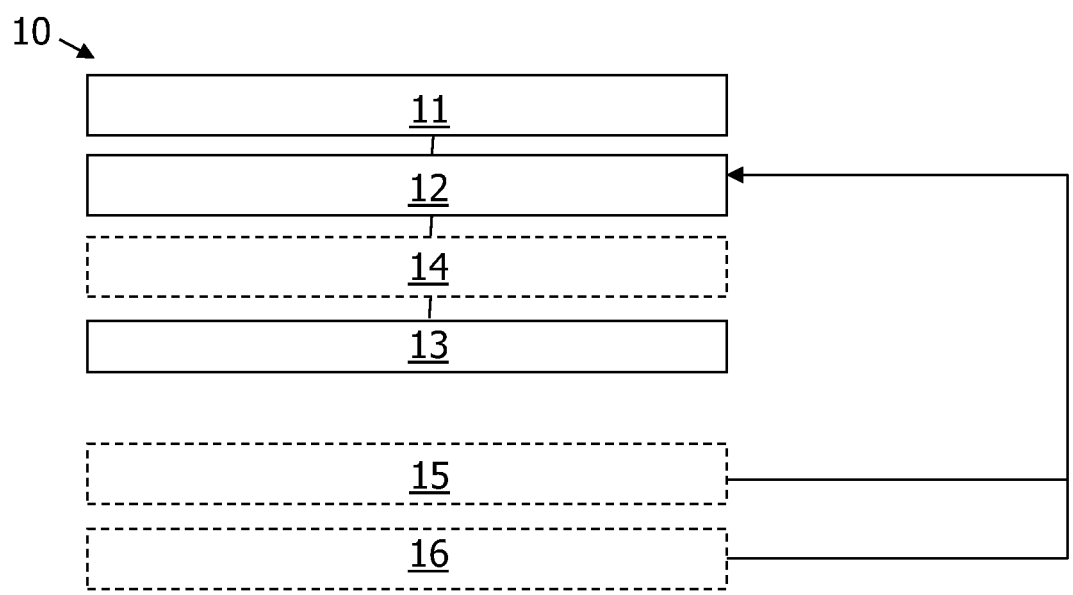
FIG. 1 illustrates a method in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to a method for testing a radius of curvature of a curved X-ray grating and/or for detecting inhomogeneities in the curved X-ray grating. The curved X-ray grating being tested by the method is a curved X-ray grating for an X-ray imaging device adapted for grating-based X-ray imaging, e.g. for phase-sensitive X-ray imaging and/or dark-field X-ray imaging. For example, the curved X-ray grating may be a curved X-ray phase grating, or may be a curved X-ray coded-aperture grating. 'Curved' refers to the phase grating being non-planar, e.g. bent along a curve in at least one direction, such as bent into, or otherwise fabricated to conform to, the shape of part of a cylindrical hull, e.g. bent in one direction along a circular curve, or the shape of a spherical shell, e.g. forming a solid angle segment of a spherical shell, e.g. bent in two orthogonal directions along circular curves.

The method comprises generating a beam of light that diverges from a source point, that propagates along a main optical axis of propagation of the beam and that has a beam profile shaped as a line. The method comprises reflecting the beam of light off a concave reflective surface of the curved X-ray grating, in which a principal axis of the concave reflective surface substantially coincides with the main optical axis, e.g. in which the principal axis is aligned with the main optical axis. The source point is at a predetermined distance from a point where the main optical axis intersects said concave reflective surface. Thus, the method may comprise positioning and aligning the source point and the curved X-ray grating in accordance with this predetermined distance and such that the main optical axis is aligned with the principal axis of the concave reflective surface. While reference is made to a 'predetermined' distance, it shall be understood by the skilled person that this distance is not necessarily numerically known a-priori, but may be determined by measurement before, during or after executing the steps of the method described further hereinbelow.

The method further comprises determining whether a projection of the reflected beam in a plane, e.g. perpendicular to the principal axis, located at or near the source point, is present outside a central region around the source point. An absence of the projection outside this central region indicates, in accordance with this method, that a radius of curvature of the concave reflective surface substantially corresponds to the predetermined distance and/or that the reflective surface is substantially homogeneously curved along a curve formed by the beam of light impinging on the concave reflective surface, e.g. a curve formed by the projection of the beam-shaped profile onto the concave reflective surface.

For example, when the radius of curvature matches the predetermined distance and the reflective surface is homogeneously curved in all points where the beam-shaped profile impinges on the concave reflective surface, the reflected light would form a projection, in a plane near the source point and perpendicular to the main optical axis, in the form of a line that has a length of less than or equal to a length $L=2*d*\tan(G/(2R))$, where $*$ refers to the multiplication operator, where tan refers to the tangent function and where G is a size of the grating, e.g. a dimension of the grating in a direction over which the longitudinal direction of the line-shaped beam profile impinging on the grating extends. Furthermore, d refer to the predetermined distance along the optical axis, e.g. the total length of the optical path followed along the optical axis, between the source point and the line of length L formed by the reflected light from the concave surface, and R refers to the bending radius of the grating. Therefore, the central region may be a region around the source point that has a maximum linear dimension, e.g. a maximum length, of $2*d*\tan(G/2R)$.

For example, the central region may be circle around the source point having a radius of $d*\tan(G/2R)$, or approximately, $d \cdot G/2R$. For example, the central region may be formed by a rectangular area, centred around the source point, having a height of $2*d*\tan(G/2R)$ (e.g. a height of about d*G/R) and a width of about the width of the beam-shaped profile, e.g. a width in the range of 1 to 10 times, e.g. in the range of 1 to 3 times, the width of the beam-shaped profile. Thus, the central region may be shaped as a linear slit, e.g. a substantially elongated rectangular area.

For example, if the X-ray grating is bent along a first direction, and substantially straight along a second direction perpendicular to the first direction, e.g. if the X-ray grating is cylindrically shaped, the central region may be a substantially elongated rectangular area having a longitudinal direction of the rectangular area substantially aligned with the first direction. For example, such central region may correspond to a rectangular slit that is provided in a projection screen for visualising the projection.

For example, if the X-ray grating is bent along both a first direction and a second direction perpendicular to the first direction, e.g. if the X-ray grating is spherically shaped, the central region may be a substantially elongated rectangular area having a longitudinal direction of the rectangular area substantially aligned with the longitudinal direction of the beam profile. Alternatively, the central region may be circular. For example, such central region may correspond to a rectangular slit or a circular hole that is provided in a projection screen for visualising the projection.

Referring to FIG. 1, a method 10 for testing a radius of curvature of a curved X-ray grating and/or for detecting inhomogeneities of the curved X-ray grating in accordance with embodiments of the present invention is illustrated. The curved X-ray grating being tested by the method, e.g. a bent X-ray grating, is a curved X-ray grating for an X-ray imaging device that is adapted for grating-based imaging, e.g. phase-sensitive X-ray imaging and/or dark-field X-ray imaging, such as a device for phase contrast and/or dark-field computed tomography, tomosynthesis, projection imaging and/or real-time and/or dynamic imaging (e.g. fluoroscopy).

The curved X-ray phase grating may be adapted in shape to conform to a wave front shape of an X-ray cone beam when emitted from a focal point at a distance from the grating, e.g. a distance substantially corresponding to a radius of curvature of the grating, and directed along the principal axis of the grating, or, at least, such adaptation of shape may be tested or verified by a method in accordance with embodiments of the present invention. For example, the curved X-ray phase grating may be curved along (part of) a spherical shell and/or a cylindrical shell.

For example, the radius of curvature of the X-ray phase grating may be tested against a predetermined value, e.g. a reference value to which the X-ray phase grating should conform. The radius of curvature may be measured by a method in accordance with embodiments. Furthermore, inhomogeneities due to local geometric deviations from a predetermined target shape, e.g. curvature, of the curved grating may be detected by a method in accordance with embodiments of the present invention. Furthermore, inhomogeneities due to local deviations from a predetermined grating pattern, e.g. a grid spacing, may be detected by a method in accordance with embodiments of the present invention.

The method comprises generating 11 a beam of light that diverges from a source point and propagates along a main optical axis of propagation of the beam. The main optical axis, i.e. the optical axis, refers to a path, e.g. an imaginary line, along which the light propagates up to a first approximation, e.g. as known in the field of optics.

For example, the beam of light may be generated by a relatively small light source, e.g. a laser diode or a light emitting diode. It is an advantage that such small light source can be substantially point-like, e.g. such as to prevent blurring of the reflected light.

The beam of light has a beam profile shaped as a line. For example, when projected on a plane that is perpendicular to a main optical axis of propagation of the beam, the pattern projected by the beam may form substantially a line or line segment. For example, the width, for example a full width at half maximum (FWHM) of the intensity profile of the beam, may be in the range of 0% to 10%, preferably in the range of 0% to 5% or even 0% to 2%, e.g. in the range of 0.0% to 0.5%, of the height, e.g. a FWHM in the height direction perpendicular to the width direction, of the beam profile. The beam profile may refer to a shape of the beam in a direction orthogonal to the direction of the main optical axis.

The beam of light may comprise light in at least part of the visible and/or ultraviolet spectrum.

In accordance with embodiments of the present invention, the beam of light may be a beam of coherent light, e.g. being at least substantially spatially coherent, for example light emitted by a laser source. For example, the beam of light may be generated by a laser line projector.

However, embodiments of the present invention are not necessarily limited to coherent light beams, e.g. the light may be generated by a compact incoherent light source, e.g. a substantially point-like light source, such as a light emitting diode, as well.

The beam of light may be a coherent light beam, e.g. a spatially coherent light beam. For example, generating 11 the beam of light may comprise generating the beam of light using a laser light source. The laser light source may emit the beam of light as a spatially coherent beam tightly focused around a main optical axis, e.g. such as to remain tightly focused over a substantial distance, e.g. such as known in the art for beams emitted by laser sources.

Generating 11 the beam of light may comprise forming the beam profile shaped as a line using an optical lens, an optical mirror or an optical assembly, e.g. arranged in the main optical axis of the beam, e.g. in the beam generated by the laser light source. For example, the optical lens may comprise a cylindrical and/or prismatic lens for generating a divergence of the beam in one direction while maintaining the spatial coherence in a direction perpendicular to both said direction of divergence and the direction of the main optical axis. For example, the cylindrical and/or prismatic lens may have a base shape that is circular, elliptic, parabolic, convex or plano-convex. Thus, the source point may refer to a focal point formed by projecting the light via the optical lens, mirror or assembly. As shall be clear to the skilled person, the base shape of the lens may also be plan concave or concave, e.g. such that the source point may refer to a virtual focal point that lies before the lens relative to a forward sense of light propagation along the main optical axis. Also, as shall be clear to the skilled person, the same or a similar beam can be produced by means of reflective optics, e.g. a mirror, instead of a lens. Furthermore, as shall be clear to the skilled person, the same or a similar beam can be produced by means of a combination of multiple optical elements, e.g. an optical assembly.

Generating the beam of light may comprise generating the beam of light from the source point in the X-ray imaging device such that this source point substantially coincides with the position of an X-ray focus of an X-ray source in the imaging device, e.g. by replacing an X-ray tube of the device by a light source adapted for this purpose. Thus, the predetermined distance advantageously corresponds to the distance between the curved X-ray phase grating and the X-ray source when the X-ray device is used for imaging. However, embodiments of the present invention are not limited thereto. For example, the grating may be removed from the X-ray device for testing.

The method comprises reflecting 12 the beam of light off a concave reflective surface of the curved X-ray phase grating. The concave reflective surface may be intended, when used in the X-ray imaging device, for being directed toward an X-ray source, e.g. in a position between the X-ray source and an image detector, to generate or analyse a phase interference pattern in an X-ray beam emitted by the X-ray source.

A principal axis of the concave reflective surface substantially coincides with the main optical axis and the source point is at a predetermined distance from a point where the main optical axis intersects the concave reflective surface.

For example, the method may comprise projecting the beam of light onto the concave reflective surface of the curved X-ray phase grating along a principal axis of the concave reflective surface.

The concave reflective surface may have a spherical concave shape or a cylindrical concave shape. The concave reflective surface may be reflective for at least a part of the visible and/or ultraviolet light spectrum. The principal axis may refer to an axis normal to the surface in a central region of the surface, e.g. at a point in the center of the surface.

The method may comprise providing the curved X-ray phase grating in the form of a curved X-ray phase grating having a concave reflective surface. Alternatively, or additionally, a method in accordance with embodiments may comprise polishing a concave surface of the curved X-ray phase grating to form the concave reflective surface. Where reference is made to 'reflective,' a reflectiveness of the grating that is sufficient to reflect at least part of the beam with sufficient power to visually perceive the reflection when impinging on a suitable projection screen is intended. For example, in at least part of the spectrum of the beam of light, the power reflected by the reflective grating may be at least 5%, preferably at least 10%, even more preferred at least 25%, even more preferred at least 50%, of the power incident on the reflective grating.

The method comprises determining 13 whether a projection of the reflected beam of light in a plane, e.g. perpendicular to the principal axis, at or near the source point, is present outside a central region around the source point. For example, the central region may have a diameter, e.g. around the source point, of less than 20 times the width (e.g. FWHM) of the line-shaped profile of the beam of light, preferably in the range of 1 to 10 times this width, e.g. in the range of 1 to 5 times the width, e.g. in the range of 1.0 to 2.0 times the width.

An absence of this projection outside the central region indicates that a radius of curvature of the concave reflective surface substantially corresponds to the predetermined distance and/or that the reflective surface is substantially homogeneously curved in points along a curve that is formed by the beam of light impinging on the concave reflective surface, e.g. by the line-shaped profile projected onto the concave reflective surface.

For example, the method may comprise providing 14 a projection screen in a plane at or near the source point, e.g. perpendicular to the principal axis. For example, 'near' the source point may refer to a distance in the range of 0 cm to 10 cm, preferably 0 cm to 5 cm, even more preferred 0 cm to 1 cm, between the plane in which the projection screen is placed and the source point, e.g. the focal point of the beam.

For example, 'near' the source point may refer to a distance in the range of 0 to 15 times the width of the line-shaped beam profile (e.g. the FWHM), preferably 0 cm to 10 times said width, even more preferred 0 to 5 times said width, e.g. 0.0 to 1.0 times said width.

The projection screen may comprise a hole through which the beam of light is projected. Thus, reflecting the beam of light off the concave reflective surface may comprise projecting the beam of light through the hole in the projection screen.

Alternatively, the projection screen may be positioned behind (w.r.t. the sense of propagation of the generated light beam) a light source for generating the light beam, and an optical lens, mirror and/or assembly may form a virtual focus point substantially on the projection screen behind the source. For example, the generated light may be shaped such as to diverge (in at least one direction, e.g. the height direction of the line-shaped beam profile) from the virtual focus point.

The projection screen may comprise an opening corresponding to the central region, e.g. such as to only visualize the projection outside the central region. This opening may advantageously also form the hole through which the beam of light is projected, but is not necessarily limited thereto. For example, alternatively, the projection screen may be transparent in one direction to allow the passage of the beam of light from the source point toward the curved grating, e.g. such as to enable a direct observation the shape and length of the reflected beam on the projection screen, the reflected beam impinging on the screen from the other sense of direction.

The projection screen may comprise a circular or rectangular opening centred around the source point, e.g. a slit-like aperture. The longitudinal direction of the rectangular opening, e.g. of the slit-like aperture, may be aligned with the lengthwise direction of the line-shaped beam profile. The projection screen may be adapted for testing gratings with a predetermined radius of curvature R and a predetermined dimension G. For example, the opening may have a maximum diameter of about $L=2*d*\tan(G/(2R))$. For example, the opening may be rectangular, or substantially elongated, having a length of about $L=2*d*\tan(G/(2R))$, e.g. about $d*G/R$, and a width in the range of 1 to 10 times, e.g. 1 to 3 times, the width of the beam profile.

The beam of light that is reflected by the reflective concave surface may project onto the source point when the distance of the source point to the concave surface, along the principal axis, is equal to, or about equal to, the radius of curvature of the concave surface and the shape of the grating surface describes a homogeneous circular arc along at least the line projected by the beam over the surface.

However, in a situation where the distance of the source point to the concave surface does not correspond to the radius of curvature, or the curved grating is inhomogeneous, a reflection can be observed on the projection screen. For example, in case of inhomogeneities in the bending of the grating, the reflected light may form a spot or irregular pattern on the projection screen, e.g. that may be easily observed. Furthermore, it is an advantage of using a line-shaped beam profile that inhomogeneities of the curved grating can be localized the line projected by the beam over the surface. Likewise, the radius of curvature of the grating can be determined in different directions over the surface of the curved grating.

However, it shall be clear to the skilled person that, instead of a projection screen, another light detecting means may also be used, such as for example a CCD camera, to detect the projected pattern of the reflected light.

The method may comprise adjusting 15 the predetermined distance between the point where the main optical axis intersects the concave reflective surface and the source point. For example the step of reflecting the beam of light off the concave reflective surface may be repeated for the adjusted distance, and the step of determining whether a projection of the reflected beam in the plane at or near the source point is present outside a central region around the source point may be repeated for the adjusted distance. Thus, the method may comprise repeatedly adjusting the predetermined distance to determine the radius of curvature of the concave reflective surface as corresponding to the adjusted distance for which the projection of the reflected beam in the plane is absent outside the central region around the source point. Additionally or alternatively, a position, amongst the tested distances, may be determined for which the projection is contained in the smallest region around the source point, and this position may be determined as the radius of curvature, or a best approximation of this radius amongst the tested distances.

The method may also comprise continuously adjusting the distance between the point where the main optical axis intersects the concave reflective surface and the source point, and continuously monitoring changes in the projection to determine the radius of curvature.

The method may also comprise rotating 16 the beam profile shaped as a line of the generated beam of light such as to evaluate the radius of curvature and/or inhomogeneities of the curved grating along different lines projected by the beam over the surface. Thus, inhomogeneities or deviations from a specified radius of curvature can be easily localized along a direction over the surface.

The method may also comprise measuring the predetermined distance, e.g. to numerically determine the radius of curvature.

Figure 2:
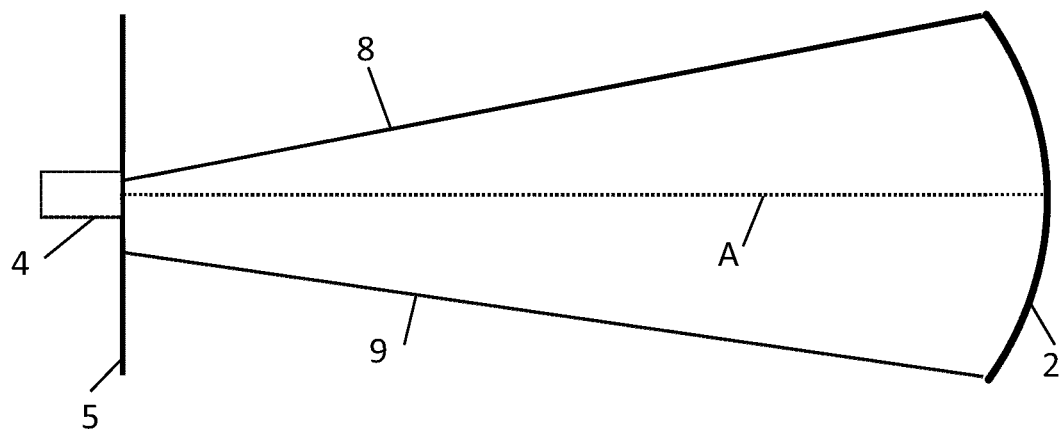
FIG. 2 illustrates operating principles of a method in accordance with embodiments of the present invention.

Referring to FIG. 2, the operation of a method in accordance with embodiments of the present invention is illustrated. A line laser source 4 generating the beam of light may be positioned at the radius of the grating 2, or at a position initially assumed to correspond to the radius of curvature of the grating. The emitted light, in case of a homogeneous grating surface and a correspondence of the distance and the radius of curvature, will be reflected 8 to the source point, e.g. to the focus of the diverging beam. In the plane of the laser, a screen 5 may be positioned such that any deviations in the reflected beam can be detected. In case there are inhomogeneities in the bending of the grating the reflected light 9 may form a large spot on the screen. This also applies if the bending radius does not correspond to the specification. In this case the actual bending radius of the grating can be determined by shifting the laser source and the screen along the optical axis in order to find the distance for which the reflected light has the minimum dimension on the screen. Thus, the method may be used to determine the actual bending radius of the grating and the bending homogeneity.

Figure 3:
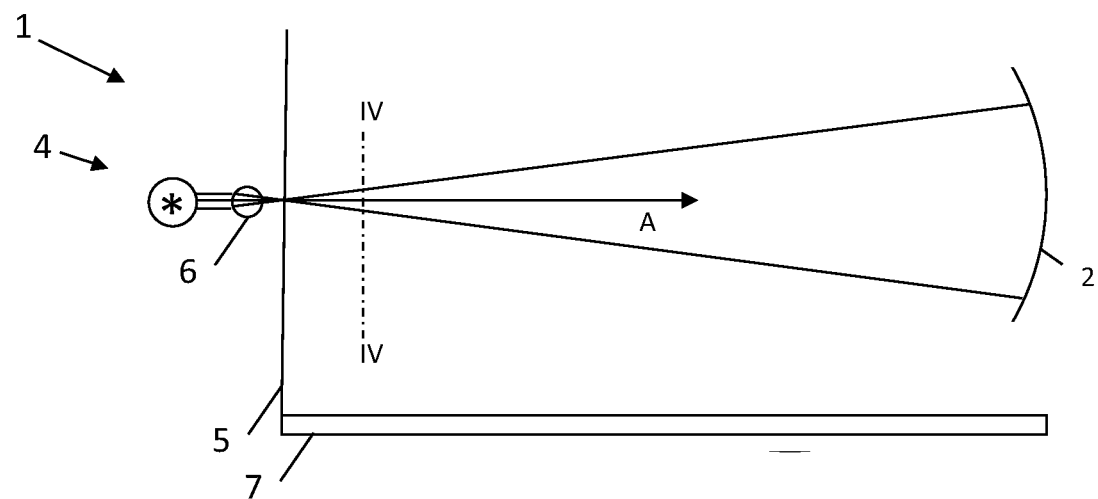
FIG. 3 shows a device in accordance with embodiments of the present invention.

Referring to FIG. 3, in a second aspect, the present invention relates to a device 1 for testing a radius of curvature of a curved X-ray phase grating 2 and/or for detecting inhomogeneities in the curved X-ray phase grating 2. The curved X-ray phase grating being tested is a curved X-ray phase grating for an X-ray imaging device adapted for phase-sensitive X-ray imaging and/or dark-field X-ray imaging.

Figure 4:
FIG. 4 illustrates an exemplary beam profile by the cross-section, along line IV-IV.

The device 1 comprises a laser light source 4 adapted for generating a beam of light that diverges from a source point, propagates along a main optical axis of propagation of the beam and has a beam profile 3 shaped as a line. For example, an exemplary beam profile is illustrated by the cross-section, along line IV-IV, in FIG. 4.

The device comprises a projection screen 5 for positioning in a plane at or near the source point to determine whether a projection of a reflected beam of light is present outside a central region around said source point, when said reflected beam of light is created by reflecting said beam of light off a concave reflective surface of the curved X-ray phase grating if a principal axis of the concave reflective surface substantially coincides with said main optical axis A.

The light source 4 may be fixed to the projection screen 5 such that the source point lies in or near said plane. Furthermore, the light source may be fixed to the projection screen 5 such that the projection screen is oriented perpendicular to the optical axis A.

The projection screen 5 may be collapsible, e.g. foldable and/or rollable, to enable transportation of the device in a compact format. For example, the device may be a portable testing device for in-field use, e.g. by a maintenance service provider.

The laser light source 4 may comprise an optical lens, an optical mirror and/or an optical assembly 6. For example, a cylindrical lens or a plano-convex cylindrical lens.

The device may comprise a rotatable mechanical coupling to rotate the optical lens, mirror and/or assembly 6 such as to rotate the line-shaped beam profile along a selectable orientation.

The laser light source 4 may be adapted for emitting light in at least part of the visible and/or ultraviolet spectrum.

The projection screen 5 may be adapted for displaying light that impinged on the projection screen, e.g. light in the visible and/or ultraviolet spectrum.

The projection screen 5 may comprise a hole through which the beam of light can be projected.

The device may comprise a distance measurement element 7 for measuring the distance between the source point and a point where the main optical axis intersects the concave reflective surface, in use of the device. The distance measurement element 7 may comprise a ruler, a tape measure, a laser distance measurement device or an ultrasonic distance measurement device. In an advantageous embodiment the device may comprise a sensor for determining the distance based on a reflection of the light emitted by the laser light source, e.g. as known in the field of laser distance measurement devices.

The device may comprise positioning and/or aligning elements for positioning and/or aligning the grating and/or the projection screen and/or the light source with respect to each other.

In embodiments, the device may be adapted for, at least temporarily, installing in the X-ray imaging device in which the grating is installed. For example, the device may comprise attachment means for installing the device to an X-ray tube housing such that the source point can be positioned to substantially coincide with an X-ray focus point of the X-ray imaging device. For example, the device may be adapted for replacing the X-ray tube temporarily during a test in accordance with a method in accordance with embodiments of the first aspect of the present invention. In an embodiment, the device may also comprise a deflector, e.g. a mirror, to reflect light from the light source. Such deflector may be adapted for positioning at or near the X-ray focus point of the X-ray imaging device, such that light projected onto the deflector by the light source is reflected along a path from the X-ray focus point toward the curved grating, e.g. such that the beam of light impinging on the curved grating appears to originate from the X-ray focus point.

The invention claimed is:

1. A method for testing a radius of curvature and/or detecting inhomogeneities of a curved X-ray grating for a grating-based X-ray imaging device, the method comprising:

generating a beam of light, wherein said beam of light diverges from a source point, propagates along a main optical axis of propagation of the beam and has a beam profile shaped as a line;

reflecting said beam of light off a concave reflective surface of the curved X-ray grating, wherein a principal axis of said concave reflective surface substantially coincides with said main optical axis and said source point is at a predetermined distance from a point where said main optical axis intersects said concave reflective surface; and determining whether a projection of said reflected beam of light in a plane at or near said source point is present outside a central region around said source point, wherein an absence of said projection outside said central region is used to indicate that a radius of curvature of said concave reflective surface substantially corresponds to said predetermined distance and/or that said reflective surface is substantially homogeneously curved along a curve formed by the beam of light impinging on the concave reflective surface.

2. The method of claim 1, wherein said plane at or near said source point is oriented perpendicular to said main optical axis.

3. The method of claim 1, further comprising using a laser light source to generate the beam of light comprising light in at least part of the visible and/or ultraviolet spectrum.

4. The method of claim 1, further comprising forming the beam profile shaped as the line using at least one of an optical lens, an optical mirror, and an optical assembly.

5. The method of claim 1, comprising polishing a concave surface of the curved X-ray grating and/or bonding a reflective material to the concave surface to form the concave reflective surface.

6. The method of claim 1, wherein said central region has a diameter, around the source point, of less than 20 times the width of the beam profile shaped as the line.

7. The method of claim 1, further comprising providing a projection screen in the plane at or near the source point.

8. The method of claim 7, wherein reflecting said beam of light off the concave reflective surface comprises projecting the beam of light through a hole in said projection screen.

9. The method of claim 1, further comprising adjusting said predetermined distance between the point where the main optical axis intersects the concave reflective surface and the source point, wherein said reflecting the beam of light off the concave reflective surface is repeated for the adjusted distance, and wherein said determining whether said projection of the reflected beam in said plane at or near the source point is present outside said central region around the source point is repeated for the adjusted distance.

10. The method of claim 9, comprising repeatedly adjusting said predetermined distance to determine the radius of curvature of the concave reflective surface as corresponding to the adjusted distance for which the projection of the reflected beam in said plane is absent outside the central region around the source point and/or for which said projection is contained in the smallest region around said source point in said plane.

11. The method of claim 10, comprising continuously adjusting said predetermined distance between said point where the main optical axis intersects the concave reflective surface and the source point, and continuously monitoring changes in said projection to determine said radius of curvature.

12. The method of claim 1, comprising rotating the beam profile shaped as the line of the generated beam of light such as to evaluate the radius of curvature and/or inhomogeneities of the curved grating along different lines projected by the beam over the concave reflective surface.

* * * * *